| United States Patent [19] | [11] Patent Number: 4,851,329 |
| Cohen et al. | [45] Date of Patent: *Jul. 25, 1989 |

[54] IMMUNOASSAY EMPLOYING OPTICAL PULSE PARTICLE SIZE ANALYSIS

[75] Inventors: Richard J. Cohen, Newton Highlands; Michael L. Broide, Cambridge; Mark S. Bowen, Medford, all of Mass.

[73] Assignee: Massachusetts Institute of Technology, Cambridge, Mass.

[*] Notice: The portion of the term of this patent subsequent to Jul. 25, 2006 has been disclaimed.

[21] Appl. No.: 871,523

[22] Filed: Jun. 6, 1986

[51] Int. Cl.$^4$ .................... C12Q 1/70; G01N 33/543; G01N 33/549; G01N 15/02

[52] U.S. Cl. .......................................... 435/5; 435/7; 436/517; 436/518; 436/520; 436/523; 436/529; 436/531; 436/533; 436/805; 436/815; 436/816; 436/817; 436/823; 356/336; 356/338

[58] Field of Search ............... 436/517, 518, 519, 520, 436/523, 529, 531, 533, 805, 806, 815, 816, 817, 823; 435/5, 7; 356/335, 336, 337, 338

[56] References Cited

U.S. PATENT DOCUMENTS

4,080,264 3/1978 Cohen et al. ................... 436/805
4,174,952 11/1979 Cannell et al. ................... 23/230

OTHER PUBLICATIONS von Schulthess, G. K. et al., *Macromolecules* 13:939 (1980).
von Schulthess, G. K. et al., *Macromolecules* 16:434 (1983).
Cohen, R. J. and Benedek, G. B., *Immunochemistry* 12:349 (1975).
von Schulthess, G. K. et al., *Immunochemistry* 13:955 (1976).
von Schulthess, G. K. et al., *Immunochemistry* 13:963 (1976).
von Schulthess, G. K. et al., *Molecular Immunology* 17:81 (1980).
"Experimental Analysis of Diffusion Controlled Coagulation Using An Optical Pulse Particle Size Analyzer", Bowen, M. S. et al., *Kinetics of Aggregation and Gelation*, (1984), pp. 185-190.
Bowen, et al., *J. of Colloid and Interface Science*, vol. 105 No. 2, p. 605, Jun. 1985.
Bowen, et al., *J. of Colloid and Interface Science*, vol. 105, No. 2, pp. 617-627, Jun. 1985.

*Primary Examiner*—Robert J. Warden
*Assistant Examiner*—Florina B. Hoffer
*Attorney, Agent, or Firm*—Hamilton, Brook, Smith & Reynolds

[57] ABSTRACT

This invention provides a means for determining the concentration of any of a wide range of antibody or antigen molecules with a high degree of specificity, accuracy and sensitivity. Antigen or antibody concentration is determined by effecting an agglutination reaction in a liquid medium and determining the cluster size distribution of agglutinated particles by optical pulse particle size analysis. The measured cluster size distribution then is compared with a standard quantitative relationship between the cluster size distribution and concentration of the antigen or antibody being tested. By this means one may specifically ascertain the absolute concentration of the antigen or antibody in question in the sample being analyzed. In addition to detecting antigen or antibody molecules, the process of this invention can be used to determine the concentration of any substance capable of specifically promoting or inhibiting an agglutination reaction such as viruses, white blood cells or the like.

24 Claims, No Drawings

IMMUNOASSAY EMPLOYING OPTICAL PULSE PARTICLE SIZE ANALYSIS

The Government has rights in this invention pursuant to Grant Number PCM-8013659 awarded by the National Science Foundation.

BACKGROUND OF THE INVENTION

Agglutination reactions involve the crosslinking of carrier particles coated with antigen (antibody) by the appropriate antibody (antigen). Agglutination reactions can also involve crosslinking of carrier particles by binding molecules other than antigens and antibodies (e.g. receptor and ligands). Agglutination reactions provide an important nonisotopic method for immunoassay of high sensitivity and specificity. The sensitivity and specificity of agglutination reactions have been substantially enhanced by application of techniques which are capable of detecting the cross-linking process at an earlier stage of the agglutination process. See, e.g., Cohen et al. U.S. Pat. No. 4,080,264 (quasi-elastic light scattering) and Cannell et al. U.S. Pat. No. 4,174,952 (light scattering intensity anistropy). By replacing the visual detection of macroscopic agglutinates containing hundreds of thousands of carrier particles as the reaction end point with an optical technique of measuring the extent of reaction—the agglutination reaction is transformed from a qualitative, and fairly sensitive immunoassay, to a quantitative and more sensitive immunoassay method.

Both the quasi-elastic light scattering spectroscopy and intensity anisotropy methods involve measurements made on bulk solution and reflect essentially different moments of the cluster size distribution of the cross-linked carrier particles. It has been estimated that the quasi-elastic light scattering spectroscopy can reliably detect agglutination when roughly 25% or more of the carrier particles are agglutinated, the intensity anisotropy method has been estimated to when as little as 5% of the carrier particles are agglutinated.

Although quasi-elastic light scattering and optical anisotropy methods of detecting agglutination provide a fairly sensitive immunoasssy, these methods cannot discriminate between light scattering from specific size clusters of carrier particles and artifacts such as dust particles or cell fragments which can cause markedly erroneous results when bulk detection techniques are used.

Another potential particle counting technique for immunoassay might be based on resistive-pulse method (or impedance). See e.g., von Schulthess, G. K., et al. *Macromolecules* 13:939 (1980); von Schulthess, G. K., et al. *Macromolecules* 16:434 (1983). The electrical, or resistive-pulse technique consists of suspending the particles in an electrolytic solvent so that as each particle enters the pore it displaces a portion of solvent resulting in a change in the pore's electrical conductivity. Since the change in conductivity i proportional to the volume of the particle, the size distribution of the sample is accumulated by sending thousands of particles through the pore. Because the measurement and subsequent signal processing is rapid, statistically meaningful distributions can be obtained in minutes.

However, resistive pulse analysis is lacking in several respects.

(1) For one, the resolution of the resistive pulse method with regard to its ability to distinguish between sizes is limited. This restricts the sensitivity of such a method because a count allocated to dimers might in fact be a monomer or vice versa.

(2) The resistive-pulse technique cannot differentiate coincidence of two monomers within the pore and the presence of one dimer because they both displace the same volume of electrolyte.

(3) The pores of the detection cell are subject to frequent plugging limiting its practical application.

Additionally, a resistive pulse analyzer requires that the particle be suspended in a high ionic strength solution in order to reduce electrical noise. Such high ionic strength may not be compatible with the formation of specific antigen antibody bonds and may nonspecifically promote, or inhibit, the clustering of the carrier particles.

The cumulative effect of the above makes the resistive-pulse analyzer an impractical means of achieving high sensitivity immunoassay based on agglutination reaction.

SUMMARY OF THE INVENTION

This invention pertains to a method for specifically and quantitatively determining antigen or antibody concentration based on an agglutination reaction.

The method employs optical pulse particle size analysis, a very sensitive technique for determining the cluster size distribution of aggregated particles based upon a proportional relationship between the intensity of light and the size of an aggregate, to characterize the cluster size distribution of agglutinated particles. The cluster size distribution of agglutinated particles is a function of the concentration of the agglutinator and thus allows determination of the concentration of agglutinator.

According to the method of this invention, an antigen or antibody to be tested is used to effect or inhibit an agglutination reaction in a liquid medium. The degree of agglutination is determined by measuring the cluster size distribution of agglutinated reaction product by optical pulse particle size analysis. The cluster size distribution then is compared with a standard quantitative relationship between the cluster size distribution of the agglutinated reaction product and the concentration of (antigen or antibody) being tested. The standard quantitative relationship can represent either the extent of agglutination after a specified reaction time or it can represent the rate of change of the cluster size distribution both of which are functions of the concentration of agglutinator. In addition to determining the concentration of antigen or antibody molecules, the process of this invention can be used to determine the concentration of any substance capable of specifically promoting or inhibiting an agglutination reaction even when the formation of antigen-antibody bonds is not involved in the agglutination process.

DETAILED DESCRIPTION OF THE INVENTION

Optical pulse particle size analysis is a technique for measuring the relative size of micron and submicron size particles. The technique can be used to determine the cluster size distribution of uniform particles suspended in a liquid medium. It is based upon the discovery of a relationship between the cluster size of aggregated particles and the intensity of light scattered from such particles as they traverse a beam of focused light. For uniform particles within a size range of about 0.03 microns to about 5-10 microns, the intensity of light scattered from the particles at sufficiently low angles is proportional to the square of the number of particles in a cluster (a proportional relationship denoted "$n^2$ dependence" where n is the number of particles in a cluster). This proportionality is independent of the orientation or configuration of the cluster.

Optical pulse particle size analysis can be carried out by a passing suspension of particles through an optical flow cell, a portion of which is illuminated uniformly by a beam of focused light such as a laser beam. As individual clusters pass through the illuminated volume each cluster scatters the incident light. Pulses of light scattered from the clusters at low angles are collected and the intensity determined. Each pulse corresponds to a cluster and the intensity of a pulse is proportional to $n^2$. Thus, the number of clusters of each size (monomers, dimers, trimers, etc.) is determined.

The theory of optical pulse particle size analysis is described in detail by Bowen et al. in Journal of Colloid and Interface Science, Vol. 105, No. 2, June 1985 which is incorporated by reference herein.

Agglutination reactions induced by specific interaction between a particulate agglutinant and an agglutinator provide a specific means for determining the concentration of agglutinator. At fixed concentrations of agglutinant, the extent of the agglutination reaction is a function of the concentration of agglutinator. The extent of agglutination provides a measurement of the concentration of agglutinator. Optical pulse particle size analysis provides an extremely sensitive means for detecting agglutination of particles, and thus provides for sensitive measurement of agglutinator concentration.

In the method of this invention, an agglutination reaction is performed in any of the modes of operation described below. The agglutination reaction may be used in several different modes to detect antigen or antibody in procedures which utilize carrier particles as follows:

(1) With antigen-coated carrier particles as agglutinant and the complementary antibody as agglutinator.

(2) With antibody-coated carrier particles as agglutinant and the complementary antigen as agglutinator.

(3) The agglutination inhibition mode with antigen-coated spheres wherein a fixed quantity of antibody is mixed with a dilution of the test sample containing the complementary antigen, inactivating a portion of the antibody. This mixture then is combined with the antigen-coated carrier particles. The degree to which the antigen in the test sample inhibits the aggregation of the carrier particles, that would otherwise have occurred, indicates the concentration of antigen present.

(4) The agglutination inhibition mode with antibody-coated spheres wherein a fixed quantity of antigen is mixed with a dilution of the test sample containing the complementary antibody inactivating a portion of the antigen. This mixture then is combined with the antibody-coated carrier particles. This degree to which the antibody present in the sample inhibits the aggregation of carrier particles, which would otherwise have occurred, indicates the concentration of antibody present.

In modes 1 and 4, the agglutination reaction serves as an antibody assay. In modes 2 and 3, it serves as an antigen assay. Mode 3 is of particular practical importance as an antigen assay since it is generally easier to obtain a sufficient quantity of purified antigen to coat the carrier particles than to obtain a similar quantity of complementary antibody. Moreover, in mode 3 the agglutination reaction serves to detect antigen molecules of any size with one or more haptenic sites. On the other hand, in mode 1 the agglutination reaction serves to detect only polyhaptenic antigens which are of sufficient size (on the order of 100 Å in diameter) to effect cross-linking of the carrier particles.

In addition, in Mode 3 (or 4), the fixed quantity of antibody (or antigen) used can be adjusted so that there is a monotonic decreasing relation between the extent of agglutination and the concentration of antigen (or antibody) being tested for. In Mode 1 (or 2), the relation between the extent of agglutination and concentration of antigen (or antibody) being tested for may be nonmonotonic. A nonmonotonic relation would require the use of one or more test sample dilution to uniquely determine the unknown concentration of antigen (or antibody).

Carrier particles can be any particles which are capable of being coated (or intrinsically coated) with antigen or antibody and which are suitable for optical pulse analysis for cluster size. The particles must meet the size criteria for which the $n^2$ dependence holds. The particles should be substantially uniform in size. The range of sizes is about 0.03 up to about 5-10 microns preferably about 0.1 up to 1 micron. The carrier particles can vary in composition, for example, they can be artificial particles such as polystyrene or latex microspheres or natural particles such as red blood cells or bacteria.

For optical pulse particle size analysis of agglutinated carrier particles, the scattered light intensity is measured over a range of angles with respect to the axis of the light beam. The lower limit is determined by the ability of the instrument employed to discriminate between scattered light and the incident light beam. The upper limit will vary depending on the size of the particles-it will generally range from about 0.1 up to about 1.0-5.4 degrees relative to the major axis of the incident beam of light for particles of the stated ranges. For particles of the preferred size range of 0.1-1 micron, the scatter lights pulses may be collected at angles up to 3 degrees from the major axis of the incident beam of light. Optimal scattering angles for particles of any selected size can be determined empirically and or by calculation. See Bowen et al. supra.

The process of this invention is applicable for accurately determining the concentration of any antigen or antibody capable of promoting or inhibiting an agglutination reaction. Representative suitable antigens or antibodies that can be tested include hormones such as human chorionic gonadotropin, luteinizing hormone, insulin, parathyroid hormone, thyroid hormone, thyroid stimulating hormone; antibiotics such a penicillin; drugs such as morphine, digoxin, barbiturates and diphenylhydantoin; and tumor, bacteria, and virus associated antigens or antibodies including hepatitis-associated antigen, carcino-embryonic antigen and HTLV-III virus or antibody. Thus, the process of this invention provides a means for measuring a very wide range of antigens and antibodies of research and clinical importance. For example, the process of this invention provides an extremely accurate means for testing for stimulation of ovulation (luteinizing hormone) and for normal and ectopic pregnancy (human chorionic gonadotropin), as well as extremely sensitive means of detecting exposure to AIDS virus.

In addition to determining the concentration of antigen or antibody molecules, the process of this invention can be used to determine the concentration of any substance capable of specifically inhibiting or promoting an agglutination reaction even where the formation of antigen-antibody bonds is not involved in the agglutination process. In this mode of operation of the invention, a fixed amount of agglutinant (the agglutinant, as before, refers to all the reagents used in fixed amount) is mixed with serial dilutions of the test sample containing the substance being tested. In such manner, one may determined the concentration of viruses capable of agglutinating red blood cells. One similarly may detect the presence of white blood cells (lymphocyte cells) capable of agglutinating such cells obtained from another individual.

The presence of antibody to any substance capable of promoting or inhibiting an agglutination reaction can also be tested. In this mode of operation, a dilution of the test sample containing the antibody being tested is first mixed with a fixed amount of the substance in question (e.g. virus). This antibody inactivates a portion of the substance. The resultant mixture is combined with a fixed concentration of the particles (e.g. red blood cells) to be agglutinated by the substance. The cluster size distribution of the agglutinated reaction produce is compared with the previously determined standard quantitative relationship between the cluster size distribution and the antibody concentration. In this manner, for example, the concentration of antibodies to particular viruses capable of inducing agglutination of red blood cells can be determined.

Inasmuch as optical pulse particle size analysis copy is capable of quantitatively detecting a much lesser degree of agglutination than previously possible, the process of this invention is capable of quantitatively detecting lower concentrations of any substance capable of promoting or inhibiting agglutination reactions as well as antibodies to such substances.

A standard quantitative relationship first is established between the cluster size distribution of the agglutinated reaction product as a function of the concentration of the antigen or antibody being assayed using fixed concentration of the agglutinant composition. Antigen or antibody-coated particles can be prepared by depositing the antigen or antibody on the surface of latex microspheres, red blood cells, bacteria or the like by means well known in the art. In addition some cells or bacteria naturally bear certain antigens or antibodies on their surface. Serial dilutions of known concentration of the antigen or antibody to be assayed for are prepared and an agglutination reaction is performed using these serial dilutions of known concentration of antigen or antibody with the fixed concentration of the agglutinant composition. The concentration of agglutinator present must be sufficiently low so that precipitation of the agglutinated particles does not occur, so that the agglutinated particles remain suspended in solution. The agglutination reaction involves the crosslinking of the coated particles to produce larger particles in proportion to the concentration of active agglutinator present. For each serial dilution of the known concentration of antigen or antibody tested, the cluster size distribution is determined for the corresponding agglutinated reaction product by means of optical pulse particle size analysis.

The standard quantitative relationship can be established (a) by measuring the cluster size distribution after a fixed incubation period during which the agglutination reaction proceeds or (b) by measuring the rate of change of the cluster size distribution. Furthermore, for the purpose of generating the standard quantitative relationship the cluster size distribution can be characterized in several ways, such as (1) measuring the number of particle dimers per unit volume (2) measuring the ratio of number of particle dimers to the number of particle monomers and (3) other measures of the cluster size distribution.

The quantitative relationship so-determined then can be employed as a standard to be applied when performing the agglutination reaction on samples containing unknown amounts of the antigen or antibody being tested. A serial dilution of each sample is prepared. The agglutination reaction is performed using one or several of these dilutions of the sample and the cluster size distribution of agglutinated particles is determined. The agglutinant composition employed to establish the standard quantitative relationship must be the same agglutinant composition employed to form the agglutinated reaction product with the antigen or antibody being tested so that an accurate comparison can be made between the standard and the unknown. The measurement of cluster size distribution of the agglutinated reaction product obtained with the antigen or antibody being tested are compared with the standard quantitative relationship cluster size distribution and the antigen or antibody concentration, and thus the original concentration of the antigen or antibody in the sample is determined. At least two sample dilutions should be analyzed by optical pulse particle size analysis in order to extrapolate the results to the standard quantitative relationship if the standard quantitative relationship displays a nonmonotonic relation to the concentration of antigen or antibody being tested. However, only one sample dilution is needed if it is known that the relationship between concentration and the measurement of the cluster size distribution employed is monotonic, at least over the expected range of concentrations.

Furthermore, it may be that substances in sample solution which promote or inhibit agglutination reactions in a nonspecific manner, could affect the shape of the cluster size distribution in a different manner than to the specific antigen or antibody being assayed for. As a result, the cluster size distribution may be analyzed to detect and correct for the presence of such nonspecific substances which might otherwise lead to an erroneous estimation of the concentration of the antigen or antibody analyte. Thus, determination of the cluster size distribution may be used to enhance the specificity as well as sensitivity, of detection of agglutination reaction.

It is also possible to use the process of this invention to measure the concentration of antigen or antibody which are naturally present on micron or submicron size particles (such as blood cells, viruses, or bacteria). In this mode, of course, the use of artificial carrier particles may not be necessary.

The method of this invention provides for extremely sensitive immunoassay. This is a result of the high intrinsic sensitivity and specificity of the agglutination reactions and the broad range of antigen and antibody for which agglutination reactions are suitable, combined with the exquisite sensitivity obtainable by optical pulse analysis of the cluster size distribution. This combination leads to extremely high sensitivity. The preferred means for determining cluster size distribution of agglutinated particles is a system described in U.S. Pat. Application Ser. No. 872,097 entitled "Improved Optical Pulse Particle Size Anallyzer" by Cohen, Broide, Bowen, filed concurrently herewith, the teachings of which are incorporated by reference. This instrument can reliably detect as few as 3 dimers for every 10,000 monomers. Thus this method is capable of detecting single molecular binding events. For characteristic antigen-antibody binding affinities, this method permits the reliable detection as few as $10^4$ (or fewer) molecules of analyte in a microliter sample. This represents an improvement of roughly 100-fold over light scattering anisotropy detection methods. In fact, this method might represent the most sensitive immunoassay method of any type.

Furthermore, the ability of optical pulse particle size analysis to identify and reject light scattering by dust or by other contaminants makes this method much superior to optical techniques which measure light scattering from bulk solution. Also, the shape of the cluster size distribution may be used to enhance specificity of the technique.

Since the method of this invention does not employ the covalent linkage of a radioisotopic label, to the species being measured, it provides substantial advantages over radioimmunoassay procedures.

The invention is illustrated further by the following Example.

EXAMPLE

This example illustrates the process of this invention for accurately determining the concentration of antibody to bovine serum albumin (BSA).

Polystyrene spheres (0.357 um dia) obtained from Dow Chemical Company are dialyzed for 48 hours against distilled water to remove surfactant. A solution 1% in polystyrene spheres and 3 mg/ml in BSA is made up in 0.02 M pH 8.0 sodium phosphate buffer. This solution is allowed to incubate overnight at 4° C. In order to remove BSA molecules that have not adhered to the polystyrene spheres, the solution is centrifuged at 15,000 rev/min for 40 min., the supernatant discarded, and the pellet resuspended in buffer. This centrifugation procedure is then repeated. The concentration of the resultant polystyrene BSA stock solution is determined by weighing the solid residue obtained by drying a measured volume of solution.

A standard quantitative relationship between the cluster size distribution and the antibody concentration is obtained in the following manner. Serial dilutions of rabbit antiserum to BSA obtainable from Calbiochem Company are prepared in a series of test tubes. To each tube are added identical aliquots of a fixed dilution of the polystyrene-BSA stock solution prefiltered through a 1 micron Nuclepore filter. The final fluid volume per tube is 2 ml and the final polystyrene-BSA concentration in each tube is chosen to come out to 11 micrograms/ml. The mixtures are allowed to incubate at room temperature for one hour. Then the samples are filtered through a 3 micron Nuclepore filter. Cluster size distributions are measured using an optical pulse particle size analyzer as described in U.S. patent application Ser. No. 872,097. See supra. The cluster size distribution is determined and the ratio R of the number of particle dimers to the number of particle monomers is computed. Absolute antibody concentration is determined by quantitative precipitation analysis by Calbiochem Company.

Two control experiments are performed to assess nonspecific agglutination. In one experiment serial dilutions of rabbit antiserum to BSA are prepared and polystyrene spheres coated with horse hemoglobin are added thereto. In the second experiment, serial dilutions of normal rabbit serum are prepared and are added polystyrene spheres coated with BSA. The cluster size distribution made on the two control systems are compared with the data obtained from a third identically prepared polystyrene-BSA, antiserum to BSA system to assess nonspecific agglutination. Nonspecific agglutinating agents present in serum can be inactivated by well-known techniques which greatly reduce or eliminate the nonspecific agglutination observed at high concentration of serum.

Comparison of measurements of R performed on two or more tubes of a dilution series of a sample of unknown antibody concentration (C) with a standard curve of R vs C enables one to determine the unknown antibody titer. In fact, the absolute antibody concentration can be determined provided that the antibody in the known and unknown solutions have similar affinities for the antigen. Choosing the first of the R vs C curves as our standard curve, we can experimentally determine the initial concentration of antibody in other samples. This determination is accomplished by (numerically) superimposing the "unknown" R vs C curve on the standard curve.

The above procedure can be modified by measuring the rate of change of R (dR/dt). Measurement of dR/dt would permit the determination of analyte concentration on the time scale of minutes rather than requiring the reaction to incubate for a prolonged period of time.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A method for determining the concentration of a substance which promotes or inhibits an agglutination reaction, comprising:
   a. determining the quantitative relationship between the cluster size distribution of an agglutinated reaction product and the known concentration of the substance being tested using a fixed concentration of an agglutinant wherein the cluster size distribution of the agglutinated reaction product is measured by optical pulse particle size analysis;
   b. mixing an unknown concentration of one or more dilutions of the substance being tested with the same agglutinant to form at least one agglutinated reaction product of the dilutions;
   c. determining the cluster size distribution of the agglutinated reaction product of the dilutions by the optical pulse particle size analysis; and
   d. comparing the cluster size distribution obtained in step (c) with the quantitative relationship determined by size (a) to determine the concentration of the substance.

2. A method of claim 1, wherein the substance being tested is an antigen which is combined with a fixed amount of its complementary antibody.

3. A method of claim 1, wherein the substance being tested is an antibody which is combined with a fixed amount of its complementary antigen.

4. A method of claim 1, wherein the substance being tested is a virus and the agglutinant comprises red blood cells.

5. A method of claim 1, wherein the substance being tested comprises an antibody to a virus and wherein the agglutinated reaction products are obtained by mixing said antibody with a fixed concentration of said virus to inactivate said antibody and adding a fixed concentration of red blood cells to said mixture to effect an agglutination reaction of said virus and said blood cells.

6. A method of claim 1, wherein lymphocyte cells obtained from one individual are used to agglutinate the substance being tested which comprises lymphocyte cells obtained from a second individual.

7. A method of claim 1, wherein the cluster size distribution is determined by measuring the concentration or numbers of carrier particle dimers.

8. A method of claim 1, wherein the cluster size distribution is determined by measuring the ratio of the number of carrier particle dimers to the number of carrier particle monomers.

9. A method of claim 1, wherein the agglutinant comprises antigen-coated carrier particles and the substance being tested is a complementary antibody.

10. A method of claim 9, wherein the substance being tested is an antibody against a virus, a bacterium, a pharmacologic agent, a tumor associated antigen, a transplantation antigen, or an antibody associated with autoimmunity.

11. A method of claim 9 wherein the carrier particle is a polystyrene or latex microsphere.

12. A method of claim 9, wherein the carrier particle is a red blood cell or a lymphocyte.

13. A method of claim 1, wherein the agglutinant comprises antibody-coated carrier particles and the substance being tested for is a complementary antigen.

14. A method of claim 13, wherein the antigen is a hormone, a polyhaptenic drug, a bacterial or viral antigen or a tumor associated antigen.

15. A method of claim 13, wherein the antigen is insulin, parathyroid hormone, luteinizing hormone, digoxin, a barbituate, morphine, diphenylhydantoin, theophylline, an antibiotic, HTLV-III antigen, hepatitis antigen or carcinoembryonic antigen.

16. A method of claim 13, wherein the carrier particle is a polystyrene or latex microsphere.

17. A method of claim 13, wherein the carrier particle is a red blood cell or a lymphocyte.

18. A method of claim 1, wherein the substance being tested in an antigen which first is mixed with a fixed concentration of its complementary antibody and the resultant mixture combined with a fixed concentration of said antigen coated on carrier particles.

19. A method of claim 18, wherein the antigen is a hormone, a mono- or polyhaptenic drug, a bacterial or viral antigen or a tumor associated antigen.

20. A method of claim 18, wherein the antigen is insulin, parathyroid hormone, luteinizing hormone, digoxin, a barbituate, morphine, diphenylhydantoin, theophylline, an antibiotic, HTLV-III antigen, hepatitis antigen or carcinoembryonic antigen.

21. A method of claim 18, wherein the carrier particle is a polystyrene or latex microscope.

22. A method of claim 18, wherein the carrier particle is a red blood cell or a lymphocyte.

23. A method of claim 1, wherein the substance being tested is an antibody which first is mixed with a fixed concentration of its complementary antigen and the resultant mixture combined with a fixed concentration of the antibody coated on carrier particles.

24. A method of claim 23, wherein the substance being tested is an antibody against a virus, a bacterium, a pharmacologic agent, a tumor associated antigen, a transplantation antigen, or an antibody associated with auto-immunity.

* * * * *